United States Patent [19]

Frazee et al.

[11] Patent Number: 4,743,613

[45] Date of Patent: May 10, 1988

[54] ESTER PRODRUGS OF DOPAMINE-β-HYDROXYLASE, INHIBITORS, COMPOSITION CONTAINING THEM, AND METHOD OF USING THEM TO INHIBIT DOPAMINE-β-HYDROXYLASE ACTIVITY

[75] Inventors: James S. Frazee, Sewell; Carl Kaiser, Haddon Heights; Lawrence I. Kruse, Haddonfield, all of N.J.; Stephen T. Ross, Berwyn, Pa.

[73] Assignee: SmithKline Beckman Corporation, Philadelphia, Pa.

[21] Appl. No.: 849,333

[22] Filed: Apr. 8, 1986

[51] Int. Cl.⁴ .................. A61K 31/415; C07D 233/84
[52] U.S. Cl. ..................................... 514/398; 548/337
[58] Field of Search ........................ 548/337; 514/398

[56] References Cited

U.S. PATENT DOCUMENTS

| | | | |
|---|---|---|---|
| 3,488,423 | 1/1979 | Doebel et al. ................... | 548/337 |
| 3,915,980 | 10/1975 | Gebert et al. ................... | 548/337 |
| 4,271,158 | 6/1981 | Mentrup et al. .................. | 514/398 |
| 4,340,738 | 7/1982 | Sipido ............................ | 548/151 |
| 4,487,761 | 12/1984 | Cole et al. ..................... | 546/296 |
| 4,532,331 | 7/1985 | Frazee et al. ................... | 548/342 |

FOREIGN PATENT DOCUMENTS

| | | | |
|---|---|---|---|
| 951 | 8/1978 | European Pat. Off. ........... | 548/337 |
| 125033 | 11/1984 | European Pat. Off. ........... | 514/398 |
| 1155580 | 6/1969 | United Kingdom ............... | 514/398 |
| 2096987 | 4/1981 | United Kingdom ............... | 548/337 |
| 2141705 | 1/1985 | United Kingdom ............... | 514/397 |

OTHER PUBLICATIONS

Iverson, et al., *Acta Cem. Scand.*, 21:279–285 (1967).
Fuller, et al., *Adv. Enzyme Regul,* 15:267–281 (1976).
Runti, et al., *Il. Farmco Ed. Sc.*, 26:260–268 (1980).
Goldstein, *Pharmacol. Rev.*, 18:77–82 (1966).
Gebert et al., *Chemical Abstracts*, 72:39275e (1970).
Hidika, et al., *Mol. Pharmacol.*, 9:172–177 (1973).

*Primary Examiner*—Henry R. Jiles
*Assistant Examiner*—Kurt G. Briscoe
*Attorney, Agent, or Firm*—Vincent L. Fabiano; Stuart R. Suter; Alan D. Lourie

[57] ABSTRACT

Compounds having the formula:

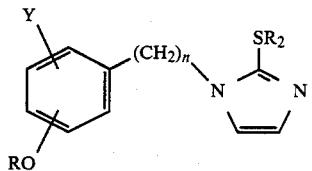

which are ester prodrugs of potent dopamine-β-hydroxylase inhibitors and thus are useful to inhibit dopamine-β-hydroxylase activity, pharmeceutical compositions including these compounds, and methods of using these compounds to inhibit dopamine-β-hydroxylase activity in mammals.

16 Claims, No Drawings

ESTER PRODRUGS OF DOPAMINE-β-HYDROXYLASE, INHIBITORS, COMPOSITION CONTAINING THEM, AND METHOD OF USING THEM TO INHIBIT DOPAMINE-β-HYDROXYLASE ACTIVITY

FIELD OF THE INVENTION

This invention relates to novel compounds that are ester prodrugs of compounds that inhibit dopamine-β-hydroxylase.

BACKGROUND OF THE INVENTION

In the catecholamine biosynthetic pathway, tyrosine is converted in three steps to norephinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409–432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159–165 and by Osumi et al., *Japan J. Pharmacol.* 23, 904 (1973).

A number of DBH inhibitors are known. These generally are divided into two classes, namely, metal chelating agents, which bind to copper in the enzyme, and phenethylamine analogues. Rosenberg et al., "Essays in Neurochemistry and Neuropharmacology," Vol. 4, edit. by Youdim et al., John Wiley & Sons, 1980, pp. 179–192, and Goldstein, *Pharmacol. Rev.* 18 (1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6-carbon side chain on a phenethylamine analogue may yield potent inhibitors.

Known DBH inhibitors include:
 (a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];
 (b) BRL 8242 [See, Claxton et al., *Eur J. Pharmacol.* 37, 179 (1976)];
 (c) 1-alkylimidazole-2-thiols [See, Hanlon et al., *Life Sci.* 12, 417 (1973); Fuller et al., *Adv. Enzyme Regul.* 15, 267 (1976)];
 (d) substituted thioureas [See, Johnson et al., *J. Pharmacol. Exp. Ther.* 168, 229 (1969)]; and
 (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl)picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoyl)methylpicolinic acid are DBH inhibitors.

Bupicomide, 5-(n-butyl)picolinamide, is reported by Ehrreich et al., "New Antihypertensive Drugs", Spectrum Publications, 1976, pg. 409–432, to be a DBH inhibitor that has antihypertensive activity.

In U.S. Pat. No. 4,532,331 a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

Friedman et al., *Psychosomatic Med.* 40, 107 (1978), report that patients treated with alpha-methyl-DOPA, guanethidine, and reserpine, but not propranolol and diuretics, have lowered DBH levels, although the significance of the observation is uncertain.

Non-specific, often toxic effects of known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

In U.S. Pat. No. 3,488,423 are disclosed compounds having the formula:

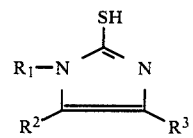

in which $R^2$ and $R^3$ can be H, and $R^1$ can be substituted phenyl. The compounds are said to have analgesic, anti-inflammatory and antipyretic properties. Gerbert et al., U.S. Pat. No. 3,915,980, disclose such compounds wherein R[1] can be phenyl or phen($C_{1-3}$)alkyl, as intermediates to imidazolyl-2-thioalkanoic acid esters.

Iverson, *Acta Chem. Scand.* 21, 279 (1967) reports compounds having the formula:

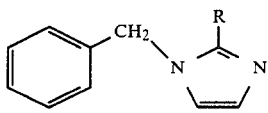

wherein R can be —$CO_2H$ or —$CH_2NHC_6H_5$, but does not report pharmaceutical uses for the compounds.

SUMMARY OF THE INVENTION

The present invention resides in the discovery that mammalian DBH is inhibited by administration of substituted hydroxyphenyl- or hydroxyphenylalkylimidazole-2-thiols esterified at the hydroxy and sulfhydryl substituents and by administration of substituted hydroxyphenyl- or hydroxyphenylalkylimidazole-2-alkylthiols esterified at the hydroxy substituent. Administration of these compounds produces prolonged DBH inhibition.

Presently preferred compounds of the invention include:

1-(4'-acetoxy-3',5'-difluorobenzyl)-2-(acetylthio)imidazole;

1-(4'-acetoxy-3'-fluorobenzyl)-2-(acetylthio)imidazole; and 1-(4'-acetoxybenzyl)-2-(acetylthio)imidazole.

The invention also is a method of inhibiting DBH activity in mammals, including humans, which comprises administering internally to a subject an effective amount of a compound of the invention.

Included in the present invention are pharmaceutical compositions comprising compounds useful in the method of the invention and a pharmaceutical carrier.

DETAILED DESCRIPTION OF THE INVENTION

The presently invented compounds that following administration to mammals inhibit DBH have the following formula:

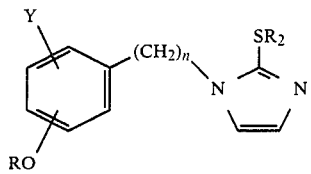

in which:

Y is hydrogen, halogen, $C_{1-4}$ haloalkyl, or any accessible combination thereof of up to four substituents, R is

wherein $R_1$ is hydrogen or $C_{1-3}$ alkyl, $R_2$ is R or $C_{1-4}$ alkyl, and n is 0–4; or a pharmaceutically acceptable salt or hydrate thereof.

As used in Formula I, $C_{1-4}$ haloalkyl is defined to include halogenated alkyl substituents having from 1 to 4 carbon atoms and 1 to 5 halogen atoms. Examples of $C_{1-4}$ haloalkyls included in Formula I comprise trifluoromethyl and pentachloroethyl.

Formula (I) includes the tautomer of the compounds wherein $R^2$ is hydrogen, that is the compounds of Formula (I) wherein the imidazole moiety has the formula:

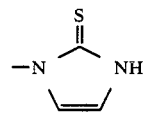

The compounds of Formula I are prepared from corresponding hydroxyphenylimidazole-2-thiols and 2-alkylthiols and hydroxyphenylalkylimidazole-2-thiols and 2-alkylthiols by known processes such as shown in Scheme I, below.

SCHEME I

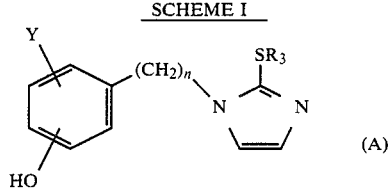

(A)

+

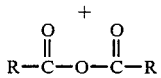

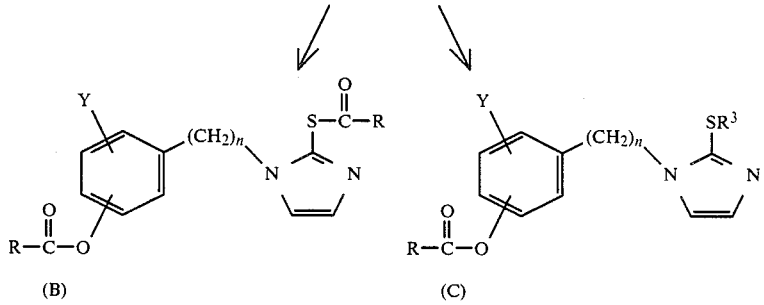

In Scheme I, Y, R, and n are as described in Formula (I) above and $R_3$ is hydrogen or $C_{1-4}$ alkyl. Scheme I illustrates esterification of starting hydroxyphenylimidazole-2-thiols and 2-alkylthiols and hydroxyphenylalkylimidazole-2-thiols and 2-alkylthiols (A) by reaction under standard conditions with an anhydride of an organic acid having from one to four carbon atoms, such as acetic anhydride. Compounds of Formula (B) wherein the hydroxy and sulfhydryl groups are esterified are produced from Formula (A) compounds in which $R_3$ is hydrogen. In contrast, Formula (C) compounds, wherein only the hydroxy group is esterified, are produced from Formula (A) compounds in which $R_3$ is $C_{1-4}$ alkyl. Compounds of Formulae (B) and (C) include all of the Formula (I) compounds of the invention.

The starting hydroxyphenylalkylimidazole-2-thiols and 2-alkylthiols are prepared from corresponding benzyl, phenyl, or phenylalkyl compounds, such as benzaldehydes, which are known and described in published references or are readily accessible by known techniques such as illustrated in Scheme II, below, in which Y is as described in Formula (I), above, $R_4$ is $C_{1-4}$ alkyl, and n is 0 to 3.

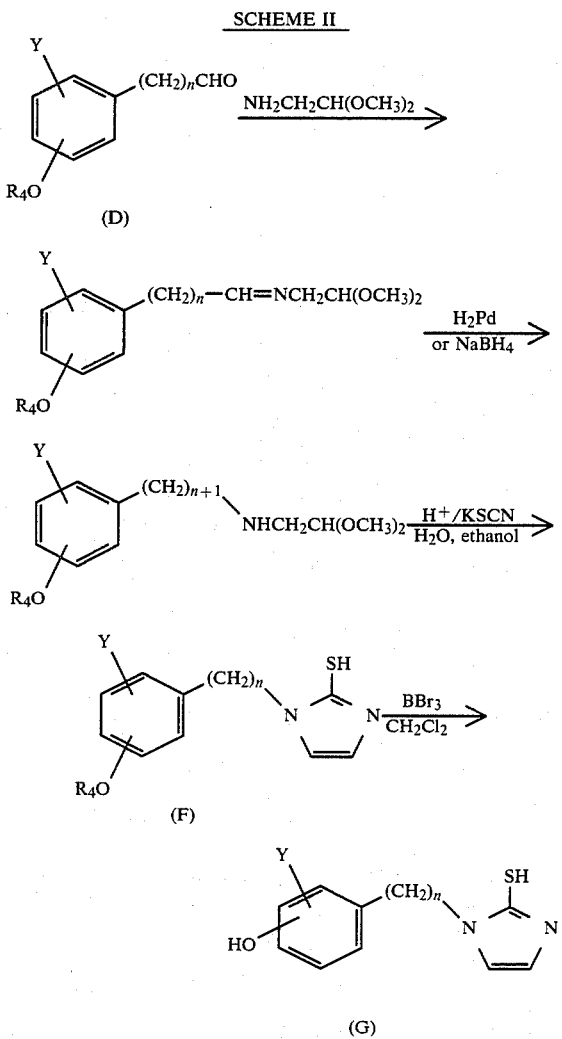

SCHEME II

Scheme II illustrates reductive amination of benzaldehydes (n is 0) (D) with an aminoacetaldehyde acetal followed by reduction by, for example, catalytic hydrogenation or treatment with a reducing agent such as $NaBH_4$, $LiAlH_4$, or $AlH_3$, to provide intermediate substituted benzylamines (E). Upon reaction with acidic thiocyanate, the intermediates (E) yield imidazole-2-thiol products (F). Deprotection of the alkoxy group with, for example, $BBr_3$ or HBr, or nucleophilic aromatic substitution with dilute hydroxide yields the starting phenolic compounds (G).

The starting compounds (A) having an alkyl group positioned on the sulfhydryl moiety preferably are prepared by allowing deprotection with for example, $BBr_3$, to proceed to formation of an alkyl bromide which alkylates the mercapto group. Alternatively, a solution or suspension of a formula (G) compound in an organic solvent, for example, methanol, tetrahydrofuran, or dimethylformamide is reacted with an alkylating agent, for example, alkyl iodide, bromide, or tosylate.

The phenolic compounds wherein n is 2, 3, or 4 preferably are prepared from intermediate substituted phenylalkylamines produced by coupling of substituted phenylalkanoic acids as the acid halides, preferably chlorides, with aminoacetaldehyde acetals and subsequent reduction.

The starting hydroxyphenylimidazole-2-thiols (n is 0) preferably are prepared by reaction of an appropriately substituted phenylisothiocyanate with an aminoacetaldehyde acetal followed by strong acid catalyzed cyclization.

The pharmaceutically acceptable acid addition salts of the compounds of the invention are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Because the compounds of Formula I upon administration to mammals, including humans, inhibit DBH activity, they have therapeutic value as diuretic, natriuretic, cardiotonic, antihypertensive and vasodilator agents, as well as antiulcerogenic agents.

A compound of the invention and its non-esterified analogue were tested for their effect in vivo on peripheral dopamine (DA) and norepinephrine (NE) levels substantially by the procedure of DaPrada and Zurcher, *Life Sciences*, 19, 1161, (1976). Groups of five spontaneously hypertensive rats were dosed orally, twice, the second dose approximately 18 hours after the first, and were sacrificed about 2 hours after the second dose. Averaged results, expressed in micrograms of DA and NE per gram of tissue are given in Table II. As the data shown in Table II demonstrate, the compound of the invention produced increases in tissue dopamine levels and alterations in tissue dopamine/norepinephrine ratios equivalent to those produced by its non-esterified analogue and by fusaric acid, a known DBH inhibitor.

TABLE II

| Compound | DA(μg/g) | NE(μg/g) | DA/NE Ratio |
|---|---|---|---|
| Control (Saline) | 0.366 | 7.10 | 0.0521 |

TABLE II-continued

| Compound | DA(μg/g) | NE(μg/g) | DA/NE Ratio |
|---|---|---|---|
| Fusaric Acid 50 mg/kg | 0.689 (2) | 5.87 | 0.118 (1) |
| 1-(4'-Hydroxybenzyl)-2-thioimidazole 50 mg/kg | 0.646 (1) | 6.50 | 0.100 (1) |
| 1-(4'-Acetoxybenzyl)-2-(acetylthio)-imidazole 50 mg/kg | 0.647 (1) | 5.85 | 0.118 (1) |

(1) $p < 0.001$
(2) $p < 0.005$

Further, the effect on blood pressure of spontaneously hypertensive rats for two of the compounds of the invention and their non-esterified analogues was measured. A solution or suspension of each of the compounds to be tested was administered intraperitoneally and blood pressure was monitored for 260 minutes using indwelling cannulae positioned in the tail arteries. In one study the effect of 50 mg/kg of 1-(4'-acetoxybenzyl)-2-(acetylthio)imidazole was compared to the same dose of 1-(4'-hydroxybenzyl)-2-thioimidazole. When compared to vehicle-treated controls, both compounds produced statistically significant blood pressure reductions approximately twenty minutes following administration; however, at 260 minutes following administration, only the blood pressure reduction produced by the esterified compound of the invention remained statistically significant.

The compounds can be incorporated into convenient pharmaceutical dosage forms such as capsules, tablets or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral products.

Doses of the present compounds in a pharmaceutical dosage unit will be an efficacious, nontoxic quantity selected from the range of 0.1-100 mg/kg of active compound, preferably 10-50 mg/kg. The selected dose is administered to a human patient in need of treatment from 1-6 times daily, orally, rectally, by injection, or continuously by infusion. Parenteral administration, which uses lower dosages is preferred. Oral administration, at higher dosages, however, also can be used when safe and convenient for the patient.

The following examples are illustrative of preparation of Formula I compounds. The examples are not intended to limit the scope of the invention as defined hereinabove and as claimed below. All temperatures and melting points (mp) are given in degrees Celsius (°C.).

EXAMPLE 1

1-(4'-Acetoxy-3',5'-difluorobenzyl)-2-(acetylthio)imidazole

A mixture of 4-methoxy-3,5-difluorobenzaldehyde (17.2 g, 0.1 mol), aminoacetaldehyde dimethyl acetal (10.5 g, 0.1 mol), and methanol (1 ml) was heated at 95° C. for 10 minutes. The resulting mixture was dissolved in ethanol (150 ml) and hydrogenated over 10% Pd on carbon (1 g) until $H_2$ uptake slowed (about 2 hours). The catalyst was filtered and the filtrate was treated with 1.5N hydrochloric acid (80 ml) and potassium thiocyanate (10.4 g, 0.11 mol). The resulting mixture was boiled until the volume was reduced to 100 ml, then it was heated a reflux an additional 1 hour and cooled to 5° C. The crystalline precipitate was filtered, washed with water, and dried. Recrystallization from ethanol gave 1-(4'-methoxy-3',5'-difluorobenzyl)-1,3-dihydro-2H-imidazole-2-thione, 72% yield, m.p. 156°-158° C.

A mixture of the 4-methoxybenzylimidazole compound (1.85 g, 0.0072 mol), produced above, in $CH_2Cl_2$ (60 ml) was treated with a solution of $BBr_3$ (7.0 g, 0.028 mol) in $CH_2Cl_2$ (10 ml). The reaction mixture was stirred for 1.5 hours at ambient temperature, cooled to 0° C. and cautiously treated with methanol (50 ml). The solvents were evaporated, and the residue was recrystallized from ethanol to yield 0.52 g (28%) of 1-(4'-hydroxy-3',5'-difluorobenzyl)-1,3-dihydro-2H-imidazole-2-thione, m.p. 213°-215° C.

A sample of 1-(4'-hydroxy-3',5'-difluorobenzyl)-1,3-dihydro-2H-imidazole-2-thione (0.98 g, 4.05 mmole) prepared as above was stirred with acetic anhydride (20 ml) and the mixture heated to reflux, giving a colorless solution. This solution was refluxed for two hours, cooled and was concentrated at the rotary evaporator. A slightly yellow oil was obtained which crystallized on cooling. The solid was dissolved in boiling ether and the solution filtered and diluted with a small amount of hexane to produce (85% yield), as a crystalline solid, 1-(4'-acetoxy-3',5'-difluorobenzyl)-2-(acetylthio)imidazole, m.p. 107°-108° C.

EXAMPLE 2

1-(4'-Acetoxy-3',5'-difluorobenzyl)-2-(methylthio)imidazole

A solution of 1-(4'-methoxy-3',5'-difluorobenzyl)-1,3-dihydro-2H-imidazole-2-thione (0.0046 mol) in 40 ml methylene chloride is treated with a solution of $BBr_3$ (0.014 mol) in 10 ml methylene chloride. After four hours methanol is cautiously added, the mixture is stirred for an additional eighteen hours and the solvents are evaporated. The residue is dissolved in water, washed with ethyl acetate, neutralized with sodium bicarbonate, and extracted with ethyl acetate. The extracts are dried ($MgSO_4$) and filtered and the solvent evaporated to yield 1-(4'-hydroxy-3'5'-difluorobenzyl)-2-(methylthio)imidazole. This compound then is substituted for 1-(4'-hydroxy-3',5'-difluorobenzyl)-1,3-dihydro-2H-imidazole-2-thione in the process of Example 1 to yield 1-(4'-acetoxy-3',5'-difluorobenzyl)-2-(methylthio)imidazole.

EXAMPLE 3

1-(4'-Acetoxyphenylpropyl)-2-(acetylthio)imidazole

The process of Example 1 beginning with 3-(4'-methoxyphenyl)-1-propionaldehyde yields 1-(4-acetoxyphenylpropyl)-2-(acetylthio)imidazole.

EXAMPLE 4

1-(4'-Acetoxy-3'-fluorobenzyl)-2-(acetylthio)imidazole

A mixture of 4-methoxy-3-fluorobenzaldehyde (15.4 g, 0.1 mol), aminoacetaldehyde dimethyl acetal (10.5 g, 0.1 mol), and methanol (1 ml) was heated at 95° C. for 10 minutes. The resulting mixture was dissolved in ethanol (150 ml) and hydrogenated over 10% Pd on carbon (1 g) until $H_2$ uptake slowed (about 2 hours). The catalyst was filtered and the filtrate was treated with 1.5N hydrochloric acid (80 ml) and potassium thiocyanate (10.4 g, 0.11 mol). The resulting mixture was boiled until the volume was reduced to 100 ml, then it was heated at reflux an additional 1 hour and cooled to 5° C. The crystalline precipitate was filtered, washed with water, and dried. Recrystallization from ethanol gave 1-(4'-methoxy-3'-fluorobenzyl)-1,3-dihydro-2H-imidazole-2-thione, 65% yield, m.p. 156°–157° C.

A mixture of the 4-methoxybenzylimidazole compound (1.72 g, 0.0072 mol), produced above, in $CH_2Cl_2$ (60 ml) was treated with a solution of $BBr_3$ (7.0 g, 0.028 mol) in $CH_2Cl_2$ (10 ml). The reaction mixture was stirred for 1.5 hours at ambient temperature, cooled to 0° C. and cautiously treated with methanol (50 ml). The solvents were evaporated, and the residue was recrystallized from ethanol to yield 1.19 g (69%) of 1-(4'-hydroxy-3'-fluorobenzyl)-1,3-dihydro-2H-imidazole-2-thione, m.p. 161°–165° C.

A sample of 1-(4'-hydroxy-3'-fluorobenzyl)-1,3-dihydro-2H-imidazole-2-thione (2.0 g, 8.9 mmole) prepared as above was heated with acetic anhydride (5 ml) for one hour on the steam bath. The reaction mixture then was treated with water (35 ml). This mixture stirred vigorously and the solid which had precipitated was filtered and dried. This was recrystallized twice from ethanol to give 1.65 g (60% yield) of 1-(4'-acetoxy-3'-fluorobenzyl)-2-(acetylthio)imidazole, m.p. 78°–80° C.

EXAMPLE 5

1-(4'-Acetoxybenzyl)-2-(acetylthio)imidazole

A mixture of 4-methoxybenzaldehye (13.6 g, 0.1 mol), aminoacetaldehyde dimethyl acetal (10.5 g, 0.1 mol), and methanol (1 ml) was heated at 95° C. for 10 minutes. The resulting mixture was dissolved in ethanol (150 ml) and hydrogenated over 10% Pd on carbon (1 g) until $H_2$ uptake slowed (about 2 hours). The catalyst was filtered and the filtrate was treated with 1.5N hydrochloric acid (80 ml) and potassium thiocyanate (10.4 g, 0.11 mol). The resulting mixture was boiled until the volume was reduced to 100 ml, then it was heated at reflux an additional 1 hour and cooled to 5° C. The crystalline precipitate was filtered, washed with water, and dried. Recrystallization from ethanol gave 1-(4'-methoxybenzyl)-1,3-dihydro-2H-imidazole-2-thione, 65% yield, m.p. 140° C.

A mixture of the 4-methoxybenzylimidazole compound (1.59 g, 0.0072 mol), produced above, in $CH_2Cl_2$ (60 ml) was treated with a solution of $BBr_3$ (7.0 g, 0.028 mol) in $CH_2Cl_2$ (10 ml). The reaction mixture was stirred for 1.5 hours at ambient temperature, cooled to 0° C. and cautiously treated with methanol (50 ml). The solvents were evaporated, and the residue was recrystallized from ethanol to yield 1.00 g (68%) of 1-(4'-hydroxy-3',5'-difluorobenzyl)-1,3-dihydro-2H-imidazole-2-thione, m.p. 188° C.

A sample of 1-(4'-hydroxybenzyl)-1,3-dihydro-2H-imidazole-2-thione (1.6 g, 7.8 mmole) prepared as above was heated with acetic anhydride (6 ml) on the steam bath for one hour. During this time a clear solution formed followed by gradual formation of a precipitate. The reaction mixture was poured into water, the mixture stirred vigorously for 30 minutes and the solid present was filtered, dried and recrystallized from ethanol twice to give 1.17 g (52% yield) of 1-(4'-acetoxybenzyl)-2-(acetylthio)imidazole, m.p. 99°–101° C.

Acidification of 1-(4'-acetoxybenzyl)-2-(acetylthio)imidazole in ethanolic solution with a solution of hydrogen chloride in diethyl ether yields 1-(4'-acetoxybenzyl)-2-(acetylthio)imidazole hydrochloride.

EXAMPLE 6

An oral dosage form for administering the presently invented compounds is produced by screening, mixing, and filling into a hard gelatin capsule the ingredients in Table III, below.

TABLE III

| Ingredients | Amounts |
| --- | --- |
| 1-(4'-Acetoxy-3',5'-difluorobenzyl)-2-(acetylthio)imidazole | 50 mg |
| magnesium stearate | 5 mg |
| lactose | 75 mg |

EXAMPLE 7

The sucrose, calcium sulfate dihydrate and benzylimidazole shown in Table IV below, are mixed in the proportions shown in Table IV and granulated with a 10% gelatin solution. The wet granules are screened, dried, mixed with the starch, talc and stearic acid, screened and compressed into tablets.

TABLE IV

| Ingredients | Amounts |
| --- | --- |
| 1-(4'-Acetoxy-3'-fluorobenzyl)-2-(acetylthio)imidazole | 100 mg |
| calcium sulfate dihydrate | 150 mg |
| sucrose | 20 mg |
| starch | 10 mg |
| talc | 5 mg |
| stearic acid | 3 mg |

EXAMPLE 8

1-(4'-Acetoxybenzyl)-2-(acetylthio)imidazole hydrochloride, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of the formula:

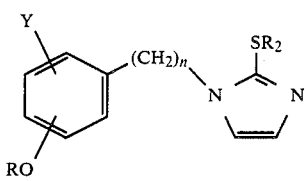

in which:
Y is hydrogen, halogen, $C_{1-4}$ haloalkyl, or any accessible combination thereof of up to four substituents;
R is

wherein $R_1$ is hydrogen or $C_{1-3}$ alkyl;
$R_2$ is R or $C_{1-4}$ alkyl;
n is 0–4; or
a pharmaceutically acceptable acid addition salt or hydrate thereof.

2. A compound of claim 1 in which:
n is 1.

3. A compound of claim 2 in which:
$R_2$ is $C_{1-4}$ alkyl.

4. A compound of claim 2 in which:
$R_2$ is R.

5. A compound of claim 4 in which:
$R_1$ is methyl.

6. A compound of claim 5 that is 1-(4'-acetoxy-3',5'-difluorobenzyl)-2-(acetylthio)imidazole.

7. A compound of claim 5 that is 1-(4'-acetoxy-3'-fluorobenzyl)-2-(acetylthio)imidazole.

8. A compound of claim 5 that is 1-(4'-acetoxybenzyl)-2-(acetylthio)imidazole.

9. A pharmaceutical composition for inhibiting dopamine-β-hydroxylase activity, comprising a pharmaceutically acceptable carrier and an amount of a compound of claim 1 sufficient to produce the inhibition.

10. A pharmaceutical composition in claim 9 in which the compound is 1-(4'-acetoxy-3',5'-difluorobenzyl)-2-(acetylthio)imidazole.

11. A pharmaceutical composition of claim 9 in which the compound is 1-(4'-acetoxy-3'-fluorobenzyl)-2-(acetylthio)imidazole.

12. A pharmaceutical composition of claim 9 in which the compound is 1-(4'-acetoxybenzyl)-2-(acetylthio)imidazole.

13. A method of inhibiting dopamine-β-hydroxylase activity in mammals, which comprises:
administering internally to a subject in need of the inhibition an effective amount of a compound of claim 1.

14. A method of claim 13 in which the compound is 1-(4'-acetoxy-3',5'-difluorobenzyl)-2-(acetylthio)imidazole.

15. A method of claim 13 in which the compound is 1-(4'-acetoxy-3'-fluorobenzyl)-2-(acetylthio)imidazole.

16. A method of claim 13 in which the compound is 1-(4'-acetoxybenzyl)-2-(acetylthio)imidazole.

* * * * *